US007353057B2

(12) United States Patent
Schiessle et al.

(10) Patent No.: US 7,353,057 B2
(45) Date of Patent: Apr. 1, 2008

(54) APPARATUS AND METHOD FOR DETECTING ATRIAL FIBRILLATION

(75) Inventors: Edmund Schiessle, Schorndorf (DE); Roland Reinhardt, Grünstadt (DE); Hans-Juergen Deeg, Hemsbach (DE); Friedhelm Soborowski, Bergisch-Gladbach (DE)

(73) Assignee: GME Rechte und Beteiligungen GmbH, Geschwenda (DE)

( * ) Notice: Subject to any disclaimer, the term of this patent is extended or adjusted under 35 U.S.C. 154(b) by 111 days.

(21) Appl. No.: 10/664,327

(22) Filed: Sep. 17, 2003

(65) Prior Publication Data

US 2004/0230109 A1 Nov. 18, 2004

(30) Foreign Application Priority Data

May 13, 2003 (EP) .................................. 03010701

(51) Int. Cl.
*A61B 5/04* (2006.01)
(52) U.S. Cl. ...................................................... 600/518
(58) Field of Classification Search ................ 600/515, 600/518, 516, 519, 521, 508
See application file for complete search history.

(56) References Cited

U.S. PATENT DOCUMENTS

| 4,750,494 | A | * | 6/1988 | King ............................. 607/14 |
| 4,896,675 | A | * | 1/1990 | Ohsuga et al. ............... 600/484 |
| 5,404,880 | A | * | 4/1995 | Throne ......................... 600/518 |
| 5,622,178 | A | * | 4/1997 | Gilham ........................ 600/523 |
| 5,682,901 | A | * | 11/1997 | Kamen ......................... 60/519 |
| 5,738,104 | A | | 4/1998 | Lo et al. |
| 6,314,321 | B1 | * | 11/2001 | Morris ........................... 607/9 |
| 6,374,138 | B1 | * | 4/2002 | Owen et al. .................... 607/5 |
| 6,416,471 | B1 | * | 7/2002 | Kumar et al. ............... 600/300 |
| 6,454,708 | B1 | * | 9/2002 | Ferguson et al. ........... 600/300 |
| 6,597,943 | B2 | * | 7/2003 | Taha et al. .................. 600/515 |
| 6,731,974 | B2 | * | 5/2004 | Levitan et al. .............. 600/515 |
| 2002/0052557 | A1 | * | 5/2002 | Griffin et al. ............... 600/515 |
| 2004/0092836 | A1 | * | 5/2004 | Ritscher et al. ............. 600/518 |

FOREIGN PATENT DOCUMENTS

EP 1 118 945 A1 7/2001
WO WO 02/24068 A1 3/2002

OTHER PUBLICATIONS

Huikuri et al., "Abnormalities in Beat-to-Beat Dynamics of Heart Rate Before the Spontaneous Onset of Life-Threatening Ventricular Tachyarrhythmias in Patients with Prior Mydocardial Infarction," Circulation, American Heart Association, Dallas, TX, Bd. 93, Nr. 10, May 15, 1996, Seiten 1836-1844, XP009009770.
Hogue et al., "RR Interval Dynamics Before Atrial Fibrillation in Patients After Coronary Artery Bypass Graft Surgery," Circulation, NR 98, Aug. 4, 1998, pp. 429-434, XP002255942.
Marciano et al., "Quantification of Poincare' Maps for the Evaulation of Heart Rate Variability," Computers in Cardiology, XX, XX, Sep. 1994, pp. 577-580, XP002166711.

* cited by examiner

*Primary Examiner*—George Evanisko
*Assistant Examiner*—Rex Holmes
(74) *Attorney, Agent, or Firm*—Brooks Kushman P.C.

(57) ABSTRACT

A lightweight, battery-operated, voltage-stabilized, bioelectronic and non-invasive measuring apparatus derives the electrical heart potentials using measuring electrodes fixed to the patient and uses electronic numerical evaluation to produce therefrom an electronic risk display for safely diagnosing atrial fibrillation at the earliest possible time in the illness.

16 Claims, 2 Drawing Sheets

APPARATUS AND METHOD FOR DETECTING ATRIAL FIBRILLATION

BACKGROUND OF THE INVENTION

1. Field of the Invention

The subject invention pertains to a method for detection of atrial fibrillation, and an apparatus suited therefor.

2. Description of the Related Art

Acquired illnesses of the heart can be divided into illnesses of the endocardium, of the myocardium, of the pericardium, and of the conduction system.

Systematic recording and consideration of the classical risk factors such as excess weight, high blood pressure or a high cholesterol level allows no more than barely 60% of the patients at risk to be identified in good time.

Invasive clinical examination methods, such as the cardiac catheter method, which is carried out 500,000 times a year in Germany alone and is associated with considerable risks, allow a reliable prediction of whether the patient examined is under threat of a heart attack at present or any other illness of the heart. One patient in a thousand dies with this method of diagnosis, however.

Non-invasive clinical methods of examination, such as electrocardiography, are not associated with such great safety risks. However, the clinical standing and reliability of this diagnostic are likewise unsatisfactory on the basis of the prior art and is too greatly dependent on the frequency with which the individual symptoms occur over time.

Electronic imaging methods, such as magnetic resonance imaging, will replace the invasive cardiac catheter method over the course of time. Electronic imaging methods allow inflammatory foci in vessels to be easily identified, and in principle to also be easily diagnosed as a result of their different tissues. However, this equipment represents a high capital investment and is also very cost-intensive in diagnostic use. Moreover, it is ill-suited to long-term observation, since patients generally cannot tolerate the relatively long time spent in the narrow tubes for accommodating the body.

Biochemical methods are generally based on blood examinations using "biomarkers". The best known method involves measuring the protein CRP, which indicates inflammatory processes in the body. This "CRP test" gives an indication allowing a patient's health risk to be estimated at least more precisely.

One good way of detecting various cardiac damage early on an electronic basis is provided by the actual heart's electrophysiological conduction system. The conduction system manifests itself differently in the individual tissue types through different electrical potential patterns, produced electrophysically by electrical polarization and depolarization.

Besides the ventricular and superventricular extrasystoles, atrial fibrillation is the most frequently occurring arrhythmia. Assuming a mean prevalence of atrial fibrillation between 0.4% and 1% of the population, there are between 330,000 and 830,000 citizens affected in Germany alone. Taking into account the fact that atrial fibrillation also increases with age and that the proportion of older people in the total population is increasing, the number of people affected will naturally also rise continually.

Atrial fibrillation is characterized by electrical excitation waves which propagate without synchronization in the atrial myocardium and result in chaotic depolarization sequences with hemodynamically ineffective atrial constrictions.

These biophysical conformities to basic laws were the starting point for development of the clinical non-invasive electrophysical diagnosis method of electrocardiography, i.e. of curve-based recording of the electrical excitation waves in the "electrocardiograms" (ECG). From the ECG it is possible to infer the heart rhythm, the heart rate, the eptopic beat and the conduction, in principle using different methods and with varying exactness. A distinction is drawn between ECG at rest, ECG under stress and long-term ECG.

In the case of atrial fibrillation, the ECG at rest shows "QRS complexes" arranged at irregular times (this is referred to as absolute arrhythmia), while the baseline has irregular fibrillation waves (the "f waves") of different amplitude and shape. Depending on the arrangement of the electrodes on the patient's body, the fibrillation waves cannot be identified with sufficient safety in all measurements, which means that the diagnosis "atrial fibrillation" can be ascertained to a sufficient extent only from the temporally irregular successions of the QRS complexes. With very fast and very slow ventricular transmission, however, the ventricular rate can appear relatively regular, giving rise to the possibility of an incorrect diagnosis of "absolute arrhythmia".

It is therefore necessary for the RR intervals for the QRS complexes to be evaluated very precisely over a relatively long period of time in order to keep the measurement deviations for rate determination in the ECG at rest within permissible limits.

The ECG under stress is a test method for estimating the heart rate under rest and stress conditions. It can thus be used to estimate the biological effectiveness of antiarrhythmics. A reduction in the heart rate does not always signify an improvement in the heart's work, however. The ECG under stress thus cannot sufficiently detect the functional cardiopulmonary stages of a patient with atrial fibrillation.

The long-term ECG is a measurement method for detecting and recording proximally occurring atrial fibrillation. There is thus the opportunity to detect both spontaneously occurring intermittent disturbances in rhythm and "trigger arrhythmia". Normal measurement times are approximately 24 to 72 hours. Long-term electrocardiography is probably the most important method of detecting and hence of diagnosing atrial fibrillation at present. Its value is in the diagnosis of symptoms which occur at least once a week. Events which occur less frequently cannot be detected using this measurement method, however. Since the unit is relatively heavy, its use on a mobile basis is limited, which means that the measurement time cannot be increased to the extent required medically.

This problem can be significantly alleviated using the "event recorder". This is an ECG recorder which, like the long-term ECG, is fixed to the patient using electrodes but has a much lower weight and physical volume. However, the recorder, weighing only a few grams, has a markedly limited storage capacity which permits ECG recording over just three minutes. The result of this is that the patient needs to press an event button when a clinical event occurs in order to start the ECG storage. Clinical experiences using the event recorder to detect atrial fibrillation are therefore also very limited. Following a recent study, a correct ECG diagnosis was able to be made in only 68% of a statistical collective with symptoms such as "palpitations", for example.

In summary, it can be said that the measurement and hence also the diagnostic certainty is too greatly dependent upon the frequency of occurrence of the corresponding symptoms. Hence, the clinical standing of this non-invasive diagnostic is not very high.

WO 02/24086 A1 discloses a system for detecting atrial fibrillation, including an evaluation circuit which calculates the distribution of RR intervals from the patient's heart potentials and compares it with at least one known distribution to generate a state signal representing the state of the patient's heart. This system involves measuring the RR intervals, forming a histogram of the ΔRR deviations, and comparing the histogram with histograms of other patients suffering from arrhythmia.

SUMMARY OF THE INVENTION

The present invention is based on the object of providing an apparatus and a method for reliable non-invasive detection of atrial fibrillation. This and other objects are achieved by repetitively obtaining a plurality of groups of n successive RR intervals from a patient's heart potentials, n being a natural number greater than 1, defining a plurality of points in an n-dimensional space of numbers, each point representing one of said groups of n successive RR intervals, to form a characteristic distribution of said points, comparing said characteristic distribution with at least one normal distribution derived from a healthy heart, and generating a state signal representing the state of the heart from said deviation.

An apparatus capable of performing these functions can be produced as a lightweight, battery-operated, non-invasive, bioelectronic measuring apparatus for electrophysically sensing bioelectrical heart potentials with numerical algorithm-assisted electronic evaluation and electronic display for safe diagnosis of atrial fibrillation at a very early time in the illness.

DETAILED DESCRIPTION OF THE PREFERRED EMBODIMENT

Figure 1:
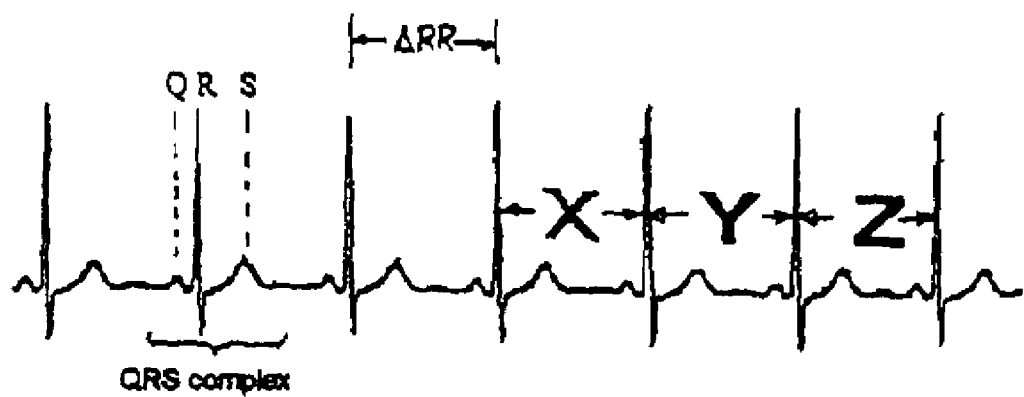
FIG. 1 shows a diagram showing the timing of the heart potentials derived using electrodes (ECG)
Figure 2:
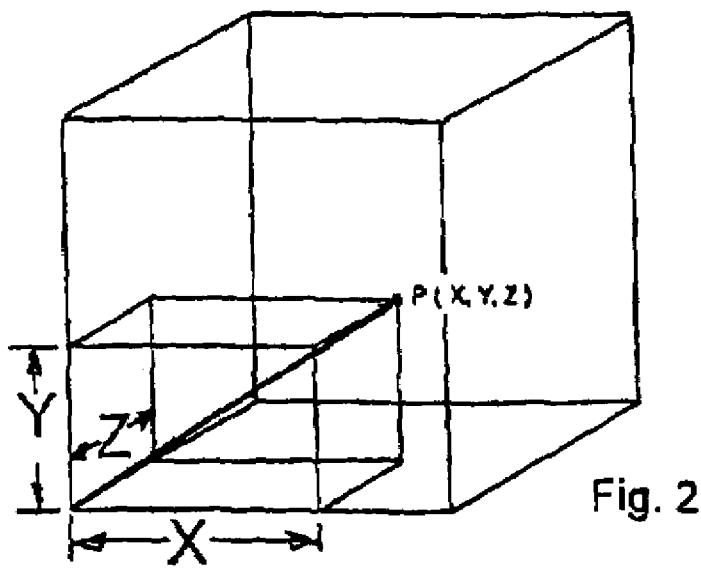
FIG. 2 shows a graphical illustration to explain a three-dimensional point structure formed from the ECG shown in FIG. 1.

In the graphical illustration of the long-term ECG, a detail from which is shown in FIG. 1, in the form of a "scatter plot", three successive RR intervals are always measured in the temporal order of the QRS complexes and are graphically represented in a three-dimensional space of numbers as a point triplet in FIG. 2, where the length of the RR intervals denoted by X, Y and Z in FIG. 1 is plotted on the three axes of the diagram and hence gives the three-dimensional position of a point P (x,y,z).

Figure 3:
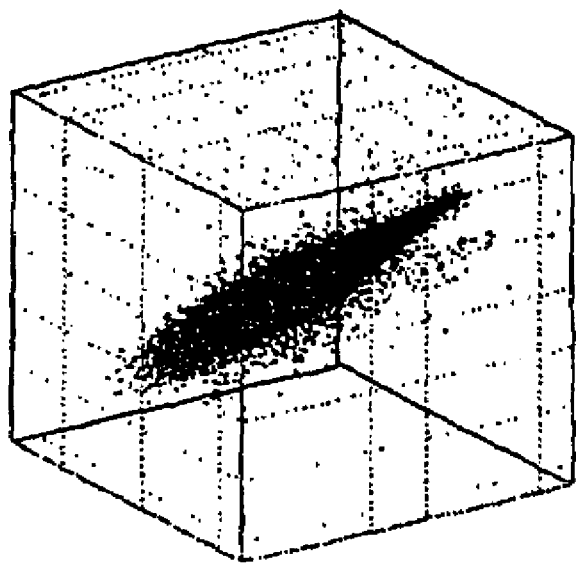
FIG. 3 shows the point structure obtained from the long-term ECG for a healthy heart using the method explained in FIG. 2.

For a healthy subject, this method of evaluation provides a three-dimensional club-shaped point structure, as illustrated in FIG. 3. By contrast, in the presence of atrial fibrillation, there is always an easily identifiable geometrical point structure, significantly different than the club geometry, in the form of a trapezium in three-dimensional orientation.

Figure 4:
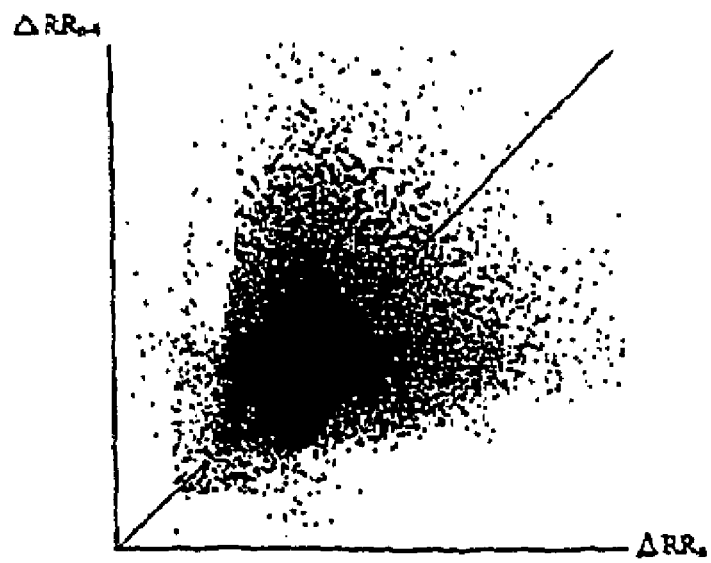
FIG. 4 shows a point structure obtained in the same way from the long-term ECG for a heart suffering from atrial fibrillation.

If only two successive RR intervals are respectively plotted on a two-dimensional diagram, then the general triangular point structure shown in FIG. 4 is formed.

This biophysical conformity to law forms the basis for the technical structure of the measuring apparatus. From the ECG, a list of the measured RR intervals is stored and these are used to produce a virtual electronic, preferably two-dimensional, scatter plot. Using a pre-programmed algorithm, the virtual scatter plot is electronically checked for the presence of a corresponding point structure (in the two-dimensional representation of the triangle structure) and if the pattern correlates with one associated with atrial fibrillation, a visual or audible indicator is given to identify the risk of possible atrial fibrillation which is imminent or is already occurring.

The measuring apparatus can be designed to be a lightweight easily portable electronic unit which does not bother the patient much during the measuring time. The measurements can be taken by the patient independently and regardless of the respective location. The display of the result of analysis is simple, which means that the patient can immediately identify his health status and can immediately go to the nearest hospital or to a corresponding specialist physician in the event of any risk.

Figure 5:
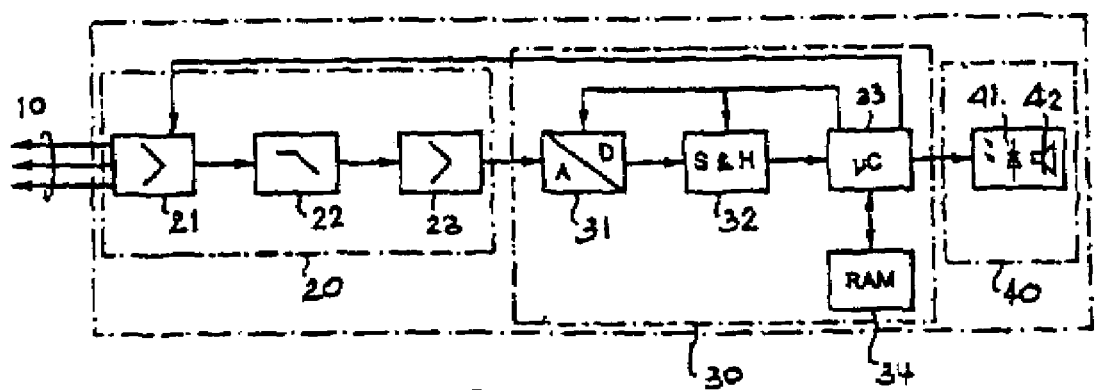
FIG. 5 shows a block diagram of an apparatus for detecting atrial fibrillation.

FIG. 5 shows the electrical block diagram for the battery-operated voltage-stabilized technical implementation of the measuring apparatus. This comprises three measuring electrodes 10 for signal derivation, a battery-powered constant (not shown) for supply voltage to the electronic assemblies, an analog block 20 for analog signal conditioning, a digital block 30 for signal processing and a display unit 40 with optoelectronic and piezoelectrical actuators. The analog block 20 comprises a highly linear, programmable-gain, broadband preamplifier 21 with very low temperature drift, a multiple electronic filter 22 and a highly linear main amplifier 23, which likewise has a very low temperature drift. The digital block 30 comprises an A/D converter 31, a sample-and-hold stage 32, a microcontroller 33 and a RAM store 34. The A/D converter 31 and the sample-and-hold stage 32 are clock-controlled by the microcontroller 33. Alternatively, the A/D converter can be integrated in the microcontroller 33. A signal from the microcontroller 33 is fed back to the control input on the preamplifier 21 in order to regulate the gain.

The three measuring electrodes 10 are used to derive the (very weak) bioelectrical potential signals from the patient's heart, and these signals are supplied directly to the preamplifier 21 via signal lines, which are shielded if appropriate. The preamplifier 21 generates from the potential signal a preamplified electrical voltage signal. The filter 22 situated between the preamplifier 21 and the main amplifier 23 is used to separate noise signal components from the useful signal components, to perform pulse shaping and to prevent antialiasing effects. The signal conditioned in this manner is re-amplified using the main amplifier 23, so that the A/D converter 31 can be actuated in line with its electrical specification.

In clocked interaction with the sample-and-hold stage 32, the A/D converter 31 generates from the analog voltage signal a corresponding digital bit sequence which is read into the memory 34 in temporal order using the microcontroller 33. The digital data material is digitally compressed and is processed, is coded, and is compared with a reference structure which is likewise stored in the memory 34.

The measuring time can be varied between the 30 and 60 minutes. When the chosen measuring time has elapsed, the result of analysis is displayed, preferably visually, using the electronic display unit 40. Since the risk of atrial fibrillation can be formally divided into four stages, the display unit 40 is designed such that it distinguishes between four different states. This can be done using a graphical LCD having four bars or a pie chart divided into quadrants. In the example illustrated in FIG. 5, four differently colored light-emitting diodes (LEDs) 41 are provided.

If the red LED 41 lights, then the occurrence of the event (atrial fibrillation) is highly likely. If the yellow LED 41 lights, the occurrence of the event is likely. If the blue LED 41 lights, then the occurrence of the event is not very likely. If the green LED 41 lights, then there is currently no risk at all of the occurrence of the event.

To ensure correct operation of the unit during the measuring time, the display unit 40 can have an integrated piezoacoustic signal generator 42 for monitoring the state of the battery, said piezoacoustic signal generator generating a beep if the battery voltage is too low and thereby requesting replacement of the battery before the measurement. Alternatively, the visual display can be furnished with a flash function.

Another opportunity for using the apparatus described here is for a routine cardiac examination as part of a general health examination in order to store the typical club-shaped point structure produced for the healthy patient and subsequently to program it into a unit as a reference structure in order to allow successful early detection.

In addition, the apparatus can be used for early detection of strokes. According to examinations by the German foundation for stroke support and on the basis of the current medical level, there is a direct link between arrhythmia/atrial fibrillation and the occurrence of a stroke. According to the Erlangen register of the German stroke support, 27% of all cerebral infarctions are based on arrhythmia.

In this context, atrial fibrillation, a form of arrhythmia, is particularly in danger of giving rise to a stroke. In this case, the heart now pumps only in an irregular manner. Owing to the fact that the atrium makes only fluttering movements and no longer contracts regularly, there is an increased risk of blood clots (emboli) forming in the atrium. If these migrate to the brain, they close off vessels and trigger a stroke.

The safe diagnosis of atrial fibrillation as early as possible in the illness has a significant influence on early detection of people who are at risk of strokes.

What is claimed is:

1. A portable apparatus for detecting atrial fibrillation by a patient, comprising:
    a) means for repetitively obtaining a plurality of groups of n successive RR intervals from the patient's heart potentials, n being a natural number greater than 1;
    b) means for producing a patient scatter plot, each point in the patient scatter plot representing one of said groups of n successive RR intervals;
    c) means for comparing the patient scatter plot with at least one normal distribution scatter plot of a healthy heart to check the patient scatter plot for the presence of a prescribed geometrical point structure corresponding to one a plurality of predefined states of not very likely to highly likely risk of atrial fibrillation;
    d) means for generating a state signal having one of a plurality of predetermined fixed values depending on the risk of atrial fibrillation from means c) such that the state signal has a first value if the risk of atrial fibrillation is not very likely, a second value if the risk of atrial fibrillation is between not very likely to a highly likely, and a third value if the risk of atrial fibrillation is highly likely; and
    e) a plurality of individually activatable visible display elements corresponding in number to the number of possible state signal values, each visible display element respectively being one of the possible state signal values, and means for activating the visible display element corresponding to the value of the state signal generated by means d);
    wherein the scatter plots are virtual scatter plots, and wherein the patient can independently identify the patient's health status by observing which visible display element is activated.

2. The apparatus of claim 1, wherein means c) further checks the patient scatter plot for the presence of a prescribed geometrical point structure corresponding to no risk of atrial fibrillation, wherein the state signal generated by means d) has a predetermined fixed value corresponding to no risk of atrial fibrillation.

3. The apparatus of claim 2, wherein the apparatus includes a further individually activatable visible display element which is activated by the state signal corresponding to no risk, visually indicating no risk of atrial fibrillation.

4. The apparatus of claim 1, wherein the individually activatable visible display elements comprise different LED visible display elements.

5. The apparatus of claim 4, wherein each LED visible display element emits a unique color upon being activated.

6. The device of claim 1, wherein the individually activatable visible display elements respectively correspond to sectors of a pie chart of an LCD display and the LCD display displays the sector corresponding to the respective state signal.

7. The apparatus of claim 1, wherein the individually activatable visible display elements respectively correspond to bars of a bar chart of an LCD display and the LCD display displays the bar corresponding to the respective state signal.

8. The apparatus of claim 1, comprising four individually activatable LED visible display elements, one LED corresponding to a state of no risk of atrial fibrillation, a second LED corresponding to not very likely risk of atrial fibrillation, a third LED corresponding to an likely risk of atrial fibrillation, and a fourth LED corresponding to a highly likely risk of atrial fibrillation.

9. The apparatus of claim 8, wherein each LED emits a different color.

10. A method for detecting atrial fibrillation and alerting a patient to three degrees of risk of atrial fibrillation, comprising
    a) repetitively obtaining a plurality of groups of n successive RR intervals from a patient's heart potentials, n being a natural number greater than 1,
    b) defining a plurality of points in an n-dimensional space of numbers, each point representing one of said groups of n successive RR intervals, to form a characteristic distribution of said points, and calculating a virtual electronic plot based on said RR intervals,
    c) comparing said virtual electronic plot with at least one normal virtual scatter plot distribution derived from a healthy heart to electronically check deviation of said characteristic distribution with said normal distribution, wherein a first relative degree of deviation corresponds to a not very likely risk of atrial fibrillation, a second relative degree of deviation corresponds to a risk of atrial fibrillation between not very likely to a highly likely, and a third relative degree of deviation corresponds to a highly likely of atrial fibrillation, and d) generating a state signal having one of a plurality of predetermined fixed values depending on the risk of atrial fibrillation from step c) such that the state signal has a first value if the risk of atrial fibrillation is not very likely, a second value if the risk of atrial fibrillation is between not very likely to highly likely, and a third value if the risk of atrial fibrillation is highly likely, and e) activating one of a plurality of individually activatable visible display elements corresponding in number to the number of possible state signal values, each visible display element respectively associated with one possible state signal value, such that the visible display element corresponding to the value of the generated state signal is activated.

11. The method of claim 10, wherein the individually activatable visible display elements comprise different LED visible display elements.

12. The method of claim 10, wherein each LED visible display element emits a unique color upon being activated.

13. The method of claim 10, wherein the individually activatable visible display elements respectively correspond to sectors of a pie chart of an LCD display and the LCD display displays the sector corresponding to the respective state signal.

14. The method of claim 10, wherein the individually activatable visible display elements respectively correspond to bars of a bar chart of an LCD display and the LCD display displays the bar corresponding to the respective state signal.

15. The method of claim 10, wherein the individually activatable visible display elements comprise four individually activatable LED visible display elements, one LED corresponding to a state of no risk of atrial fibrillation, a second LED corresponding to low risk of atrial fibrillation, a third LED corresponding to an intermediate risk of atrial fibrillation, and a fourth LED corresponding to a highly likely of atrial fibrillation.

16. The method of claim 10, wherein each LED emits a different color.

* * * * *

UNITED STATES PATENT AND TRADEMARK OFFICE
CERTIFICATE OF CORRECTION

PATENT NO. : 7,353,057 B2
APPLICATION NO. : 10/664327
DATED : April 1, 2008
INVENTOR(S) : Edmund Schiessle et al.

It is certified that error appears in the above-identified patent and that said Letters Patent is hereby corrected as shown below:

Column 8, Line 14, Claim 15:

Delete "low" and insert -- not very likely --.

Column 8, Line 15, Claim 15:

Delete "intermediate" and insert -- likely --.

Signed and Sealed this

Eighth Day of July, 2008

JON W. DUDAS
*Director of the United States Patent and Trademark Office*